(12) United States Patent
Shaner et al.

(10) Patent No.: US 11,926,816 B2
(45) Date of Patent: Mar. 12, 2024

(54) MATERIALS AND METHODS FOR CHARACTERISING DIASTATIC ACTIVITY

(71) Applicant: OMEGA YEAST LABS, LLC, Chicago, IL (US)

(72) Inventors: Lance Shaner, Chicago, IL (US); Laura Burns, Chicago, IL (US)

(73) Assignee: OMEGA YEAST LABS, LLC, Chicago, IL (US)

( * ) Notice: Subject to any disclaimer, the term of this patent is extended or adjusted under 35 U.S.C. 154(b) by 421 days.

(21) Appl. No.: 17/152,473

(22) Filed: Jan. 19, 2021

(65) Prior Publication Data

US 2021/0222116 A1 Jul. 22, 2021

Related U.S. Application Data

(60) Provisional application No. 62/963,374, filed on Jan. 20, 2020.

(51) Int. Cl.
*C12N 1/16* (2006.01)

(52) U.S. Cl.
CPC ............ *C12N 1/16* (2013.01); *C12N 2500/34* (2013.01)

(58) Field of Classification Search
CPC .............................. C12N 1/16; C12N 2500/34
See application file for complete search history.

(56) References Cited

PUBLICATIONS

Matheson et al., "Whole-Genome Sequence and Variant Analysis of W303, a Widely-Used Strain of *Saccharomyces cerevisiae*", G3 (Bethesda). Jul. 2017; 7(7): 2219-2226 (Year: 2017).*
Chuang et al., Coupling Yeast Golden Gate and VEGAS for Efficient Assembly of the Violacein Pathway in *Saccharomyces cerevisiae*, Methods Mol. Biol., 1671:211-225 (2018).
Gallone et al., Domestication and Divergence of Saccharomyces cerevisiae Beer Yeasts, Cell, 166(6):1397-1410.e16 (2016).
Jones, Regulation of amino acid and nucleotide biosynthesis in yeast, The Molecular Biology of the Yeast *Saccharomyces*: Metabolism and Gene, 2:181-299 (1982).
Korbie et al., Touchdown PCR for increased specificity and sensitivity in PCR amplification, Nature Protocols, 3:1452-1456 (2008).
Krogerus et al., A deletion in the STA1 promoter determines maltotriose and starch utilization in STA1+ *Saccharomyces cerevisiae* strains, Appl. Microbiol Biotechnol., 103(18):7597-7615 (2019).
Laake et al., Extraction of genomic DNA from yeasts for PCR-based applications, Biotechniques, 50(5):325-328 (2011).
Lin, Formulation and testing of cupric sulphate medium for wild yeast detection, J. Inst. Brewing, 87(3):151-154 (1981).
Linder et al., The ADE2 gene from Saccharomyces cerevisiae: sequence and new vectors, Gene, 95(1):91-98 (1990).
Meier-Dornberg et al., *Saccharomyces cerevisiae* variety diastaticus friend or foe?—spoilage potential and brewing ability of different *Saccharomyces cerevisiae* variety diastaticus yeast isolates by genetic, phenotypic and physiological characterization, FEMS Yeast Res., 18(4): foy023 (2018).
Mitchell et al., Versatile genetic assembly system (VEGAS) to assemble pathways for expression in *S. cerevisiae*, Nucleic Acids Res., 43(13):6620-6630 (2015).
Myasnikov et al., The *Saccharomyces cerevisiae* ADE1 gene: structure, overexpression and possible regulation by general amino acid control, Gene, 109(1):143-7 (1991).
Yamauchi et al., Rapid Methods for Detecting *Saccharomyces diastaticus*, a Beer Spoilage Yeast, Using the Polymerase Chain Reaction, J. Am. Soc. Brew. Chem., 56(2):58-63 (1998).

* cited by examiner

*Primary Examiner* — Ruth A Davis
(74) *Attorney, Agent, or Firm* — MARSHALL, GERSTEIN & BORUN LLP (57) ABSTRACT

The disclosure provides a culture plate comprising medium which supports microbial growth and comprises a dextrin comprising four or more glucose units linked by $\alpha(1\rightarrow 4)$ glycosidic bonds as a sole carbon source. The culture plate comprises a first zone inoculated with a sta- *S. cerevisiae* strain which produces a pigment upon sugar fermentation, and a second zone adjacent to the first zone and which is not inoculated with a microbe. The disclosure further provides a method of using the culture plate to characterize microbial diastatic activity.

21 Claims, 6 Drawing Sheets
(5 of 6 Drawing Sheet(s) Filed in Color)

FIGURE 1. Growth on Nutrient Rich Media (YPD)

FIGURE 2. Growth on Diastaticus Selection Medias

FIGURES 3A-3D. Measurements of Dextrin III Degradation in STA+ strains.

FIGURE 4A-4B. Maltodextrin Co-culture Assay for STA+ strain supported growth of W303

FIGURE 4C-4D. Maltodextrin Co-culture Assay for STA+ strain supported growth of W303

FIGURE 5A-5D. Beer Refermentation with STA+ Strains

MATERIALS AND METHODS FOR CHARACTERISING DIASTATIC ACTIVITY

CROSS-REFERENCE TO RELATED APPLICATIONS

This application claims the priority benefit under 35 U.S.C. § 119(e) of U.S. Provisional Patent Application No. 62/963,374, filed Jan. 20, 2020, the disclosure of which is incorporated herein by reference in its entirety.

FIELD OF THE DISCLOSURE

The instant disclosure relates to methods of identifying and characterizing diastatic contaminants in a sample.

BACKGROUND

Diastatic strains of *Saccharomyces cerevisiae* are widely used industrial brewing strains. Previously referred to as *S. cerevisiae* var. *diastaticus*, these strains are traditionally used in Belgian beer styles such as Saison, Belgian Golden Strong, and Biere de Garde styles. Among 1,011 *S. cerevisiae* isolates sequenced from wild, clinical, and industrial sources, diastatic yeast were only found within a subset of industrial beer yeast and small group of human isolates in French Guiana. These diastatic yeasts represent a rare subpopulation of *S. cerevisiae* that are ubiquitous in the brewing industry, but are far less common among the overall *S. cerevisiae* population.

Diastatic strains are capable of fermenting dextrins. Dextrins are mixtures of D-glucose polymers derived from grain starches in brewing, representing about 20-25% of total wort carbohydrates. The genetic determinants for diastatic activity in *S. cerevisiae* are the STA1/STA2/STA3 genes. These genes are unlinked and reported positions are on Ch. V, II, and XIV, respectively. The contribution of each of these gene loci remains unresolved; thus, these genes are referred to collectively as the STA genes. The STA genes arose from a gene fusion event between the FLO11 and SGA1. SGA1 is non-essential, intracellular $\alpha$-1,4 glucoamylase expressed under sporulation conditions and is typically inactive in industrial brewing strains. FLO11 encodes a GPI-anchored cell surface glycoprotein that is induced in late stages of fermentation and plays a major role in flocculation. The STA genes contain the upstream regulatory sequence of FLO11 along with the FLO11 signal sequence for secretion fused to the $\alpha$-1,4 glucoamylase of SGA1. In diastatic strains, the chimeric STA genes are expressed during fermentation to produce secreted $\alpha$-1,4 glucoamylase, which leads to degradation of dextrins in wort and, ultimately, hyperattenuated beers with low residual extract and elevated ethanol.

While being widely used in the brewing industry, diastatic strains of *S. cerevisiae* represent one of the major contamination threats to packaged beer. Cross contamination of traditional ale or lager with a diastatic strain poses risks of hyperattenuation and re-fermentation, resulting in increased production of alcohol and $CO_2$. In packaged product, diastatic contamination can result in gushing beer and exploding bottles/cans.

Within the STA+ strains, there is considerable variation in attenuation levels. Recent results from Krogerus et al. (*Applied Microbiology and Biotechnology*, 103, 7597-7615 (2019)) identified and characterized a 1,162 bp deletion upstream of the STA genes. This deletion removes key upstream activating sequences (UAS) and results in a decrease in STA gene expression and diastatic activity. For simplicity, strains containing both intact STA genes and the 1,162 bp deletion in the STA promoter are referenced herein as STA+/uas−.

Deletion of UAS can be detected by PCR and used as a screening tool for brewers when characterizing known diastatic yeast or an unknown diastatic contaminant. Though PCR genotyping provides a valuable characterization and screening tool for brewers, there are significant limitations. First, there is considerable variability in diastatic activity among STA strains that is not explained solely by the 1,162 bp deletion in the STA promoter. Second, PCR genotyping is susceptible to user errors and extraneous variables that can lead to false-positive and false-negative results. Third, PCR results can only confirm the presence of DNA and does not determine whether the source of the DNA is a living cell. Lastly, there is the potential for a brewing contaminant to be diastatic due to another determinant unrelated to STA that has yet to be identified and, as such, is not detected using PCR.

Unfortunately, traditional microbiological methods for detection of diastatic strains of *S. cerevisiae* do not provide a clear readout for diastatic activity of the contaminant. The most widely used STA+ selection media, Lin's Cupric Sulfate Medium (LCSM), is permissive for strains that have elevated copper resistance. This strongly correlates to the STA+ strains within the Beer II Group, as these are more closely related to industrial wine strains that have adapted resistance to copper-based fungicides. While copper resistance and diastatic activity often appear to be correlated, they have independent mechanisms.

Another difficulty in detecting diastatic strains of *S. cerevisiae* is the low CFU tolerances in co-culture. In contaminated beer, a few STA+ cells can secrete the Sta1 enzyme and provide fermentables for the remaining live cells in the product. In some highly diastatic strains that release more Sta1 enzyme, the tolerances will be even lower.

There remains a need in the art for materials and methods for detecting and characterizing microbial diastatic activity, including activity of *S. cerevisiae* diastatic strains.

BRIEF SUMMARY

The disclosure provides a culture plate comprising medium which supports microbial growth (e.g., growth of *Saccharomyces cerevisiae*) and comprises a dextrin comprising four or more glucose units linked by $\alpha(1\rightarrow4)$ glycosidic bonds as a sole carbon source. The culture plate comprises a first zone inoculated with a sta− *S. cerevisiae* strain which produces a pigment upon sugar fermentation, and a second zone adjacent to the first zone and which is not inoculated with a microbe.

The disclosure further provides a method of characterizing microbial diastatic activity, including diastatic activity of *Saccharomyces cerevisiae*. The method comprises inoculating the second zone of the culture plate described herein with a microbe sample, incubating the plate under conditions which allow growth of *S. cerevisiae* and the microbe, and identifying growth of the sta− *S. cerevisiae* strain, wherein growth of the sta− *S. cerevisiae* strain indicates the presence of diastatic activity in the microbe sample. In various aspects, the microbe is *S. cerevisiae*. Optionally, the method further comprises detecting pigmented colonies in the first zone of the culture plate, wherein the presence of pigmented colonies indicates the presence of diastatic activity in the microbe (e.g., *S. cerevisiae*) sample.

Unless otherwise defined herein, scientific and technical terms used in connection with the present application shall have the meanings that are commonly understood by those of ordinary skill in the art. Further, unless otherwise required by context, singular terms shall include pluralities and plural terms shall include the singular. The terms "comprising," "having," "including," and "containing" are to be construed as open-ended terms unless otherwise noted. If aspects of the disclosure are described as "comprising" a feature, embodiments also are contemplated "consisting of" or "consisting essentially of" the feature. The use of any and all examples, or exemplary language (e.g., "such as") provided herein, is intended merely to better illustrate the disclosure and does not pose a limitation on the scope of the disclosure unless otherwise claimed. No language in the specification should be construed as indicating any non-claimed element as essential to the practice of the disclosure. Other than in the operating examples, or where otherwise indicated, all numbers expressing quantities of ingredients or reaction conditions used herein should be understood as modified in all instances by the term "about" as that term would be interpreted by the person skilled in the relevant art.

Recitation of ranges of values herein are merely intended to serve as a shorthand method of referring individually to each separate value falling within the range and each endpoint, unless otherwise indicated herein, and each separate value and endpoint is incorporated into the specification as if it were individually recited herein.

DESCRIPTION OF THE FIGURES

The patent or application file contains at least one drawing executed in color. Copies of this patent or patent application publication with color drawing(s) will be provided by the Office upon request and payment of the necessary fee.

FIGS. 3A-3D illustrate measurements of dextrin III degradation in STA+ strains.

FIGS. 4A-4D depict various aspects of the dextrin co-culture assay described herein, wherein a STA+ strain supported the growth of indicator strain, W303.

FIGS. 5A-5D illustrate various aspects of the beer re-fermentation study described in the Example.

DETAILED DESCRIPTION

The instant description provides improved tools and methods for the detection and risk assessment of microbial contaminants which pose a risk of re-fermentation (e.g., STA+ contaminants) in yeast samples. The disclosure provides, e.g., a plate-based, co-culture assay that clearly identifies presence of a diastatic strain in a sample and, in various aspects, determines the degree of diastatic phenotype in, e.g., brewing strains and brewing contaminants. The co-culture screening assay can be used to determine the diastatic activity of an unknown contaminant or as a complementary approach to verify PCR results. For example, as explained above, not all STA+ strains hyperattenuate beer or pose a re-fermentation risk. PCR methods can detect STA+ sequences, but cannot distinguish between highly diastatic strains that pose a significant risk to bottled products versus weak diastatic strains that pose no significant risk. As such, practitioners may needlessly discard product out of fear of exploding bottles/cans where the risk of re-fermentation is relatively low. The tools and methods described herein allow functional characterization of diastatic potential of prospective contaminants to avoid unnecessary discard of product.

The disclosure provides a culture plate comprising medium which supports microbial growth (e.g., the growth of *Saccharomyces cerevisiae*) and comprises a dextrin comprising four or more glucose units linked by α(1→4) glycosidic bonds as a sole carbon source. The culture plate comprises a first zone inoculated with a sta− *S. cerevisiae* strain which produces a pigment upon sugar fermentation (also referred to herein as an "indicator strain"), and a second zone adjacent to the first zone and which is not inoculated with a microbe (e.g., yeast).

Culture plates suitable for microbial culture are widely commercially available. A plate may be made out of any of a number of materials, typically plastic or glass, and may comprise any suitable shape (round, square, or other shapes). The tools and methods of the disclosure are not dependent on a particular culture plate so long as the plate is suitable for microbial (e.g., yeast) culture, although certain materials and formats may be more preferable for certain embodiments of the disclosure. The culture plates are of a sufficient size to allow growth of at least two different microbial samples (e.g., an indicator strain and a yeast sample to be characterized) in distinct zones. In various aspects, the first and second zones do not overlap. In this regard, the culture plate comprises a first zone inoculated with a sta− *S. cerevisiae* indicator strain. The second zone is not inoculated with a microbe (e.g., yeast) and is located adjacent to the first zone within sufficient distance such that diastatic activity of a microbe (e.g., yeast) sample grown on the second zone can impact growth of the indicator strain.

For example, in various aspects, the second zone does not significantly overlap with the first zone (to reduce cross-contamination of the different strains to the extent possible), but is sufficiently close such that the products of dextrin degradation mediated by a diastatic (e.g., STA+ yeast) strain are available to be metabolized by the indicator strain, resulting in pigment generation. The distance and format of the zones for a particular embodiment of the disclosure may be determined by one of ordinary skill in the art based on, e.g., plate size, media content, particular strains used, and the like. Representative examples of suitable formatting of a first zone and a second zone are illustrated in FIGS. 4B and 4C.

The culture plate comprises medium which supports the growth of a microbe (if not *S. cerevisiae*) and *S. cerevisiae* and further comprises a dextrin comprising four or more glucose units linked by $\alpha(1\rightarrow 4)$ glycosidic bonds as a sole carbon source (i.e., the sole carbon containing composition that yeast metabolizes). Media which support the growth of *S. cerevisiae* and other microbes are well known in the art. The medium is generally a solid or gel which comprises all (or substantially all) of the nutrients necessary to support the growth of, e.g., *S. cerevisiae*, including, for example amino acids, minerals, vitamins, and the like (e.g., peptone, yeast and/or malt extract, agar, a nitrogen source (e.g., Yeast Nitrogen Base (YNB)), a sulfate source, a copper source, etc.). A suitable medium comprises, for example, YNB+ nitrogen, SC-Complete mix (commercially available from, e.g., Sunrise Science Products), and agar, which is further described in the Example.

The term "carbon source" refers to a carbon containing composition (e.g., compound, mixture of compounds) that a microbe (e.g., yeast) may metabolize. Dextrin comprising four or more glucose units linked by $\alpha(1\rightarrow 4)$ glycosidic bonds is the sole carbon source in the culture plate medium. Dextrin may be produced from starch or glycogen using any of a variety of methods. Source material for dextrin production may be, for instance, corn, potato, rice, arrowroot, wheat, milo, sago, or tapioca starch. Heat, acid, alkali, and/or enzymes (e.g., amylases) are typically employed to produce dextrin from source material. In various aspects the disclosure, the dextrin is maltodextrin, dextrin commercial type I, dextrin commercial type II, dextrin commercial type III, potato starch, corn starch, tapioca starch, amylose, or amylopectin. In an exemplary embodiment, the dextrin is maltodextrin. If the microbial sample to be tested comprises a STA+ yeast strain which secrets Sta1 protein, the enzyme degrades the dextrin and supports the growth of the sta− indicator strain. The materials and methods of the disclosure are not dependent on the use of a STA+ yeast strain; the microbe may be, e.g., bacteria or mold suspected of producing amylase or glucoamylase, which degrades dextrin and supports the growth of the sta− indicator strain. An amount of dextrin is provided in the medium to support the metabolism of a diastatic microbe (e.g., directly support the STA+ strain) and produce sufficient degradation products to support the sta− strain, and optionally produce sufficient levels of pigment by the indicator strain to detect and/or characterize diastatic activity. For example, the medium optionally comprises about 0.1%-20% dextrin (e.g., about 0.5%-10% dextrin, about 1-8% dextrin, about 1-4% dextrin, about 1-3% dextrin, about 2-4% dextrin, or about 2% dextrin).

In one aspect of the disclosure, the culture plate comprises Synthetic Complete medium (0.67% YNB+ nitrogen, 0.2% SC-Complete mix, 2% agar) and 2% maltodextrin.

The first zone of the culture plate is inoculated with a sta− *S. cerevisiae* strain which produces a pigment upon sugar fermentation (the "indicator strain"). The terms "inoculated," "plated," or "plating" are used interchangeably to reference establishing a yeast culture on the culture plate. Yeast cells may be diluted in cell culture media then added to the plate using any suitable aseptic laboratory technique. Yeast cells may be plated at any suitable concentration and/or densities, depending on the particular embodiment. Optionally, the amount of indicator strain provided on the culture plate is one isolated yeast colony or about $10^6$ to about $10^9$ cells Optionally, the sta− *S. cerevisiae* strain comprises the ade2-1 allele, a deletion or inactivating mutation in ade1, or a deletion or inactivation mutation in ade2. Cells carrying the ade2-1 allele form red colonies due to the accumulation of the intermediate metabolite P-ribosylaminoimidazole carboxylate (red pigment) in vacuoles. *S. cerevisiae* with inactivating mutations in ade1 or ade2, or which lack all or part of the genes such that functional gene product is not generated, also result in pigmented colonies. See, e.g., Stotz & Linder, "The ADE2 gene from *Saccharomyces cerevisiae*: sequence and new vectors," Gene, 95(1), 91-98 (1990); Myasnikov et al., "The *Saccharomyces cerevisiae* ADE1 gene: structure, overexpression and possible regulation by general amino acid control," Gene, 109(1), 143-7 (1991); Jones and Fink, "Regulation of amino acid and nucleotide biosynthesis in yeast" pp. 181-299 in The Molecular Biology of the Yeast *Saccharomyces*: Metabolism and Gene Expression, Strathern et al. (Eds.) Cold Spring Harbor, N.Y.: Cold Spring Harbor Laboratory Press) (each reference is hereby incorporated by reference in their entirety). In various aspects, the sta− *S. cerevisiae* strain is W303 MATa {leu2-3,112 trp1-1 can1-100 ura3-1 ade2-1 his3-11,15}.

Alternatively, the sta− *S. cerevisiae* strain optionally expresses a non-native pigment. By "non-native pigment" is meant a pigment that is not naturally found in wild-type yeast. In this regard, the sta− *S. cerevisiae* strain may be engineered to produce, e.g., plant or bacterial pigment to produce pigmented colonies when growth is supported by a STA+ strain. Examples of non-native pigments include, but are not limited to, b-carotene, violacein, and RFP. Examples of materials and methods for generating a yeast strain that expresses a non-native pigment are further described in, e.g., Chuang et al., "Coupling Yeast Golden Gate and VEGAS for Efficient Assembly of the Violacein Pathway in *Saccharomyces cerevisiae*," Methods Mol Biol., 1671, 211-225 (2018); Mitchell et al., "Versatile genetic assembly system (VEGAS) to assemble pathways for expression in *S. cerevisiae*," Nucleic Acids Res., 43(13), 6620-6630 (2015) (each reference is hereby incorporated by reference in their entirety).

The disclosure further provides a method of characterizing microbial diastatic activity. The microbe may be any microorganism (e.g., yeast, bacterium, or mold), which optionally is suspected of producing amylase or glucoamylase (or other enzyme with similar activity that would result in re-fermentation due to degradation of dextrins). In various aspects of the disclosure, the microbe is yeast, optionally *Saccharomyces cerevisiae*. The method comprises inoculating the second zone of the culture plate described herein with a microbe sample (e.g., *S. cerevisiae*-containing sample), incubating the plate under conditions which allow growth of the microbe and *S. cerevisiae*, and identifying growth of the sta− *S. cerevisiae* strain. Growth of the sta− *S. cerevisiae* strain can be determined using any suitable means, such as visual observation. Growth of the sta− *S.* cerevisiae strain indicates the presence of diastatic activity in the microbe sample (e.g., *S. cerevisiae* sample). In various aspects, the method further comprises detecting pigmented colonies in the first zone of the culture plate, wherein the presence of pigmented colonies indicates the presence of diastatic activity in the microbe sample (e.g., *S. cerevisiae* sample). Pigmented colonies may be observed visually with the naked eye or utilizing microscopy, if needed.

By employing an indicator strain that produces pigmented colonies, it is possible to differentiate between, e.g., robust growth (red), intermediate growth (red-white gradient), and slow growth (white) of the sta− strain, thereby allowing visual estimation of diastatic activity of a microbial (e.g., yeast) sample and, by extension, risk of re-fermentation or hyperattenuated beer. The co-culture assay described herein is associated with significant technical advantages. Unlike PCR, which merely provides a "positive/negative" result for the presence of STA- and UAS- related nucleic acid sequences, the co-culture assay of the disclosure allows functional characterization of diastatic potential of prospective contaminants, which is a more meaningful result for industrial brewing to estimate risk associated with contaminant diastatic activity.

The method comprises inoculating the second zone of the culture plate with a microbe sample. In various aspects, the sample is a *S. cerevisiae* sample, which is optionally taken from yeast stocks, yeast slurries, yeast propagations, or enriched fermentation product (e.g., beer) samples, although the method of the disclosure is not dependent on particular sample source. Microbe (e.g., yeast) cells in the sample may be diluted in cell culture media then added to the plate using any suitable aseptic laboratory technique. Optionally, the amount of microbe (e.g., yeast) sample cells applied to the culture plate is about 1 to about $10^9$ (e.g, about 10 to about $10^9$). The amount of microbe (e.g., yeast) sample cells applied to the culture plate may be about 10, about $10^2$, about $10^3$, about $10^4$, about $10^5$, about $10^6$, about $10^7$, about $10^8$, or about $10^9$, as well as any range of endpoints referenced herein (e.g., the amount of microbe sample cells applied to the culture plate may be at least about 10, at least about $10^2$, at least about $10^3$, at least about $10^4$, at least about $10^5$, at least about $10^6$, at least about $10^7$, or at least about $10^8$ and/or no more than about $10^2$, no more than about $10^3$, no more than about $10^4$, no more than about $10^5$, no more than about $10^6$, no more than about $10^7$, no more than about $10^8$, or no more than about $10^9$).

The plates are incubated under conditions which allow growth of the microbe and *S. cerevisiae*. Suitable conditions for *S. cerevisiae* culture (as well as other microbe cultures) are well known in the art. In various aspects, the plate is incubated at about 8° C.-45° C. (e.g., about 20° C.-45° C., about 25° C.-40° C. or about 28° C.-32° C., or about 30° C.) aerobically. The plate is incubated for a period of time, for example, between about 24 hours and about one month, to allow the indicator strain and the microbe (e.g., yeast) sample to grow if a diastatic strain (e.g., STA+ strain with diastatic activity) is present in the sample. In some embodiments, the plate is incubated at least about 3 days and no longer than about a month (e.g., about 30 days). For example, in various aspects, the plate is incubated between about 5 days and about 21 days, between about 7 days and 14 days, between about 7 days and 28 days, between about 8 days and about 17 days, between about 10 days and about 14 days. In various aspects, the plate is incubated for about one week (about seven days). In various aspects, the plate is incubated for about one month (about 30 or 31 days). Longer incubation periods, e.g., greater than one month, and shorter incubation periods, e.g., less than 24 hours, are also contemplated.

Various embodiments of the disclosure are described in the following numbered paragraphs:

1. A culture plate comprising medium which supports microbial growth and comprises a dextrin comprising four or more glucose units linked by α(1→4) glycosidic bonds as a sole carbon source, wherein the culture plate comprises a first zone inoculated with a sta− *S. cerevisiae* strain which produces a pigment upon sugar fermentation, and a second zone adjacent to the first zone and which is not inoculated with a microbe.

2. The culture plate of paragraph 1, wherein the dextrin is maltodextrin, dextrin commercial type I, dextrin commercial type II, dextrin commercial type Ill, potato starch, corn starch, tapioca starch, amylose, or amylopectin.

3. The culture plate of paragraph 2, wherein the dextrin is maltodextrin.

4. The culture plate of any one of paragraphs 1-3, wherein the medium comprises 0.1%-20% dextrin.

5. The culture plate of paragraph 4, wherein the medium comprises 0.5%-10% dextrin.

6. The culture plate of paragraph 5, wherein the medium comprises 1-4% dextrin.

7. The culture plate of paragraph 6, wherein the medium comprises 2% dextrin.

8. The culture plate of any one of paragraphs 1-7, wherein the medium comprises YNB+ nitrogen, SC-Complete mix, and agar.

9. The culture plate of any one of paragraphs 1-8, wherein the sta− *S. cerevisiae* strain comprises the ade2-1 allele, a deletion or inactivating mutation in ade1, or a deletion or inactivation mutation in ade2.

10. The culture plate of any one of paragraphs 1-8, wherein the sta− *S. cerevisiae* strain expresses a non-native pigment.

11. The culture plate of any one of paragraphs 1-8, wherein the sta− *S. cerevisiae* strain is W303 MATa {leu2-3,112 trp1-1 can1-100 ura3-1 ade2-1 his3-11,15}.

12. The culture plate of any one of paragraphs 1-11, wherein the microbe is yeast.

13. The culture plate of paragraph 12, wherein the yeast is *S. cerevisiae*.

14. A method of characterizing microbial diastatic activity, the method comprising inoculating the second zone of the culture plate of any one of paragraphs 1-13 with a microbe sample, incubating the plate under conditions which allow growth of *S. cerevisiae* and the microbe, and identifying growth of the sta− *S. cerevisiae* strain, wherein growth of the sta− *S. cerevisiae* strain indicates the presence of diastatic activity in the microbe sample.

15. The method of paragraph 14, further comprising detecting pigmented colonies in the first zone of the culture plate, wherein the presence of pigmented colonies indicates the presence of diastatic activity in the microbe sample.

16. The method of paragraph 14 or paragraph 15, comprising incubating the culture plate for at least three days.

17. The method of any one of paragraphs 14-16, comprising incubating the culture plate for no longer than about one month.

18. The method of paragraph 16, comprising incubating the culture plate for about one week.

19. The method of paragraph 16, comprising incubating the culture plate for about one month.

20. The method of any one of paragraph 14-19, wherein the microbe is yeast.

21. The method of paragraph 20, wherein the yeast is *S. cerevisiae*.

All references, including publications, patent applications, and patents, cited herein are hereby incorporated by reference to the same extent as if each reference were individually and specifically indicated to be incorporated by reference and were set forth in its entirety herein.

The following Example is given merely to illustrate the present disclosure and not in any way to limit its scope.

Example

Diastatic yeast are a major contamination risk to packaged beer. Brewery quality control programs rely on microbial selective methods and PCR detection of the STA genes, however there is a wide functional range of diastatic activity that remains unresolved by these current methods. This Example describes a comprehensive analysis of *diastaticus*-selection medias using a collection of STA+ strains. Additionally, several functional assays are described which confirm the variation in diastatic activity across STA+ strains and show a clear correlation with earlier onset and increasing strength in strains that contain an intact STA promoter.

In particular, diastatic *S. cerevisiae*-selective medias for diastatic *S. cerevisiae* were evaluated by screening a STA+ collection on commercially available LCSM and FPDM. Then, an optimized LCSM composition was developed. Next, two independent functional assays were developed to test for diastatic activity in the brewery environment, which confirmed a range of diastatic activities. The onset and strength of diastatic activity both increased in STA+/UAS+ strains relative to STA+/uas− strains. The plate-based assay developed as described herein determines the degree of diastatic phenotype in brewing strains and brewing contaminants.

The assay correlates highly with STA+/UAS+ strains as being stronger diastatic contaminants; however, the plate-based assay resolves variation in diastatic activity that cannot strictly be determined through PCR genotyping. Lastly, this Example provides evidence that the assays described herein correlate well with re-fermentation studies in packaged product and can be used to assess risk of a potential diastatic contaminant. Taken together, this work presents new, validated methods to detect diastatic activity to aid the brewing industry with identifying and preventing contamination of their products.

Materials and Methods

Industrial brewing strains used in this study are referenced by their commercial name supplied by Omega Yeast labs, LLC. A summary of the strains is provided in Table 1.

TABLE 1

Yeast Strains

| Strain Name | Description | STA (5A/6B genotyping) | UAS (intact 1162 bp of promoter) |
|---|---|---|---|
| OYR-001 | MATa {leu2-3, 112 trp1-1 can1-100 ura3-1 ade2-1 his3-11,15} | − | − |
| OYL-006 | British Ale I | − | − |
| OYL-019 | Belgian Ale D | + | − |
| OYL-025 | Bavarian Wheat | + | − |
| OYL-026 | French Saison | + | + |
| OYL-027 | Belgian Saison I | + | − |
| OYL-033 | Jovaru | + | + |
| OYL-039 | Biere de Garde | + | + |
| OYL-040 | Belgian Dark Ale | + | − |

TABLE 1-continued

Yeast Strains

| Strain Name | Description | STA (5A/6B genotyping) | UAS (intact 1162 bp of promoter) |
|---|---|---|---|
| OYL-042 | Belgian Saison II | + | − |
| OYL-055 | Vermont Farmhouse Ale | + | − |
| OYL-056 | Belgian Golden Strong Ale | + | + |
| OYL-088 | West Coast Ale I | − | − |
| OYL-112 | Swiss Lager | + | + |
| OYL-200 | Tropical IPA | + | − |
| OYL-205 | Specter Ale | + | − |
| OYL-500 | Saisonstein's Monster | + | + |
| OYL-501 | Gulo Ale | + | + |

PCR Genotyping of STA1 and the 1162 bp deletion in the STA1 promoter: Multiplex PCR was performed using the previously published primers SD-5A and SD-6B for STA1 gene 868 b.p. fragment (Yamauchi et al., *J Am Soc Brew Chem.* 1998; 56:58-63) and STA1_UAS_Fw and STA1_UAS_Rv for the STA1 UAS 599 b.p. promoter fragment (Krogerus et al., App/Microbiol Biotechnol. 2019; 103(18):7597-7615). Genomic DNA was prepared using the Looke et al. method (Biotechniques 2011; 50(5):325-328). Briefly, a small amount of cells was resuspended in 50 μL of 0.2 M LiAC/1% SDS buffer solution and heated to 70° C. for 5 min. The solution was precipitated with 200 μl of 100% EtOH at −20° C. for 10 min. DNA was pelleted at 13 k rpm for 3 min, rinsed with 70% EtOH and air dried. The pellet was resuspended in 50 μl of DNAse/RNAse-free water (GIBCO). PCR reaction included 2 μl of DNA, 1 μM of each primer, and 2× Gotaq mastermix (Promega). Touchdown PCR was performed (Korbie et al., *Nature Protocols* 2008; 3:1452-1456) and reactions were separated on a TAE 1% agarose gel. Resulting PCR status was reported as UAS+ and STA+ if the corresponding 599 b.p. and 868 b.p. bands were detected.

Preparation of STA+ Selection Media and Serial Dilution Plating for Comparing Commercial Formulations: Media formulations selected for comparison: prepared LCSM (0.4% yeast extract, 0.2% dried malt extract, 0.2% yeast peptone, 0.1% dipotassium ortho-phosphate, 0.05% ammonium sulfate, 0.06% cupric sulfate, 1% dextrose, 2% agar), commercial LCSM (Weber Scientific), and FPDM (Weber Scientific). Plates were autoclaved together using a solid load setting for 20 min (Hiyarama HVA-110) and poured 24 hours, 48 hours or 96 hours prior to plating serial dilutions. Serial dilutions of 1:6 were performed from a starting concentration of 1 million cells/ml with 5 μl of diluted cells spotted. Plates were imaged after 3 days at 30° C.

Dextrin degradation liquid medium preparation: Liquid DDM (dextrin degradation medium) is based on maltodextrin as a carbon source coupled with a pH indicator dye that changes color as yeast cells metabolize the maltodextrin. Components include maltodextrin at 2% (w/v; Sigma-Aldrich, #419672), yeast nitrogen base with ammonium sulfate at 0.67% (w/v, Sunrise Science Products, #1501-100), $K_2HPO_4$ at 0.014% (w/v; J. T. Baker, #4012-05), and Brom Cresol Green at 0.022% (w/v; BBL, #04-198). The medium was brought to a pH value of 5.8-6.0 using 1 M HCl. Medium was then vacuum filter sterilized with a 0.2 μm PES filter. The prepared medium is a deep blue, but turns green and then yellow as yeast cells degrade and metabolize maltodextrin (concurrently decreasing the medium pH). Buffer concentration was optimized to prevent background metabolism from non-diastatic strains from being able to induce a color change in the medium.

DDM colorimetric assay: The ability of strains to degrade dextrin was tested using DDM. Isolated colonies grown on YPD agar were directly inoculated into 500 µl of dextrin media in a sterile 1.5 mL microcentrifuge tube. Tubes were rotated at 70 r.p.m. at room temperature for up to 20 days. Color change was assessed in two different ways. First, a visual estimation was performed to determine whether the color was blue, green, or yellow. This estimation was used for graphical displays. Second, color change was quantified by removing 100 µL of the sample to a 96-well plate and measuring absorbance at 620 nm in a UV-Vis plate reader (Biotek Epoch2). As each reaction contained 500 µL, the A620 measurement could not be taken as frequently as the visual estimate. Biological triplicates were performed using a separate colony for each replicate.

DDM detection limits in pure and mixed culture: To measure the lower limit of detection, three strains were selected based on their behavior when a full colony was inoculated into the media. These included a strain that changed DDM to yellow within 48 hours (OYL-026, French Saison), a strain that changed the media to yellow within one week (OYL-027, Belgian Saison I), and a strain which took longer than one week to change the media to yellow (OYL-019; Belgian Ale D). To test the lower limit of detection in pure culture, 10-fold serial dilutions of each strain were prepared to inoculate DDM with 100-1,000,000 cells. To test the lower limit of detection in mixed culture, each of the three strains above were mixed in different ratios with a non-*diastaticus* strain (OYL-006, British Ale 1). In both cases, visual and quantitative assessment of color change was performed as described above.

Absorbance-Based Assay for Dextrin Degradation: Individual colonies from YPD plates (1% yeast extract, 2% peptone, 2% glucose, 2% agar) were inoculated into YPEG liquid medium (1% yeast extract, 2% peptone, 2% ethanol, 3% glycerol)+2% Dextrin III (MP Biomedicals) and incubated overnight at 23° C. with agitation. Cultures were removed from the shaker and incubated without agitation at 23° C. for 4 weeks. Dextrin degradation was measured at day 7, 14, 21 and 28. Each week, 200 µl of the culture was removed and briefly centrifuged to remove cells. Twenty µl of the supernatant was transferred to a 1 cm cuvette with 1 ml of 0.04% Lugol's iodine solution (10% potassium iodide, 5% iodine). Measurements for absorbance were collected at 540 nm and 680 nm using a UV-vis spectrophotometer (Thermo Scientific GENESYS 180). The UV-vis spectrophotometer was blanked with 0.04% Lugol's iodine. A non-*diastaticus* control (OYL-088) was included, as well as an uninoculated control as negative controls. Each *diastaticus* strain was normalized to the OYL-088 measurement to determine the percentage of Dextrin III remaining. The results are averaged from eight biological replicates. Reported for each strain is the week at which Dextrin III levels were reduced to <50% of starting Dextrin III (as determined by the negative control OYL-088).

Maltodextrin Plate Assay for *Diastaticus*-Supported Growth: Maltodextrin plates were prepared with SC (Sunrise Science; 0.67% YNB+ nitrogen, 0.2% SC-Complete mix, 2% agar) and 2% maltodextrin (Spectrum Chemical). Strains grown on YPD plates were patched to the maltodextrin plates adjacent to diploid W303. The plates were incubated at 30° C. aerobically for 1 month of observation. Strains were scored based on the following criteria: – (no difference to compared to OYL-088), + (growth of STA+ strain), ++ (growth of STA+ strain and supported growth of W303), and +++ (growth of STA+ strain with red pigment in W303). Limit of detection assays were performed with a spread plate of W303 and spotting of 20 I test culture. The test cultures were from saturated propagations. The STA1+ strain was serially diluted 1:10 into a non-*diastaticus* control strain (OYL-088). The corresponding concentration of cells is $2 \times 10^6$ cells/spot STA+ strain ($10^0$) down to 2-3 cells/spot STA+ strain and $2 \times 10^6$ cells OYL088 (10-6).

Bottle Re-fermentation and Analysis: Strains were inoculated into 2 ml YPEG liquid media and incubated overnight at 23° C. with agitation. Saturated cultures were inoculated into bottles of IPA at 3 million cells/bottle. Crowns were removed from bottles, the culture was inoculated and the bottles were recrowned. Negative controls included a non-*diastaticus* strain (OYL-088) and a mock inoculation with water. A set of 10-fold dilutions was also performed with OYL-026, OYL-027, OYL-042, and OYL-056. The starting 3 million cells/bottle was serially diluted 1:10 in sterile water and the resulting dilutions were inoculated into bottles. Bottles were incubated at 30° C. for one month. The residual extract was measured with a density meter and alcohol by volume were measured using a DMA™ 4500 M and Alcolyzer ME (Anton Paar). Dissolved $CO_2$ was measured using a piercing device (Pentair) and c-DGM gehaltemeter (Pentair). Each inoculation was performed in biological triplicate.

Results and Discussion

Optimization and comparison of STA+ selection medias: To address the prevalence of false positives and negative rates from brewers, an improved *diastaticus* (STA+) selection media was prepared. A goal was to achieve the highest recovery rate of STA+ strains with minimal growth of sta– strains. The most widely used STA+ selection media, Lin's Cupric Sulfate Medium (LCSM), is permissive for strains that have elevated copper resistance. This strongly correlates to the STA+ strains within the Beer II Group, as these are more closely related to industrial wine strains that have adapted resistance to copper-based fungicides (Galone et al., *Cell*. 2016; 166(6):1397-1410.e1316). It is worth noting that while copper resistance and diastatic activity appear to be often correlated, they have independent mechanisms. A recently introduced STA+ selection media, Farber Pham *Diastaticus* Media (FPDM), is suggested to be superior to LCSM for the detection of STA+ strains and additionally allows for differentiation of STA+ strains by starch degradation and a zone of clearance. The exact composition of this medium has not been reported.

LCSM was initially prepared according to the original published formulation (Lin, *J. Inst. Brewing*, 87(3), 151-154 (1981)). Ideal concentrations of cupric sulfate and dipotassium ortho-phosphate were then determined using STA+ and sta– brewing strains set forth in Table 1. Concentrations of 0.06% cupric sulfate and 0.01% dipotassium ortho-phosphate were ideal for selective growth of the STA+ strains (data not shown).

Figure 1:
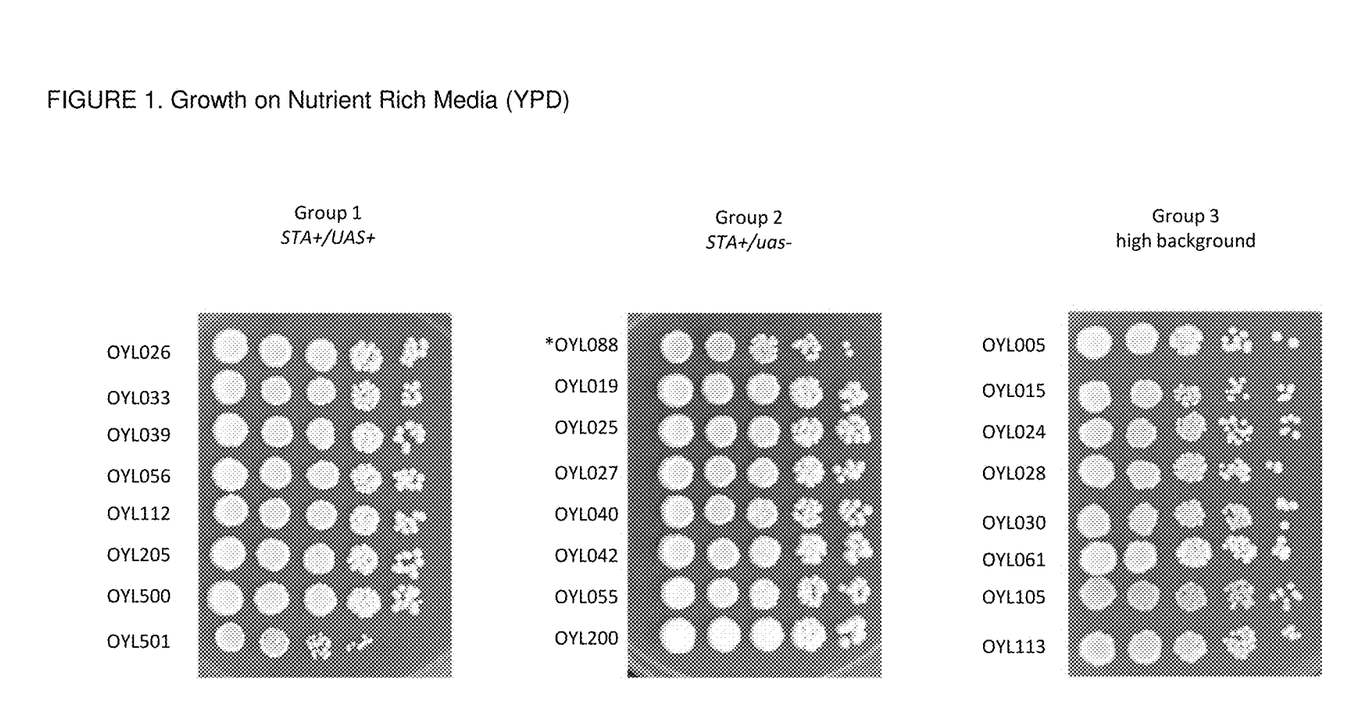
FIG. 1 depicts growth from serial dilutions as described in the Example: Group 1=STA+/UAS+; Group 2=STA+/uas−; and Group 3=high background strains plated on YPD media. Serial dilutions of 1:6 were performed from a starting concentration of 1 million cells/ml. *OYL-088 is included as a control and does not contain STA1. Plates were imaged after 3 days at 30° C.
Figure 2:
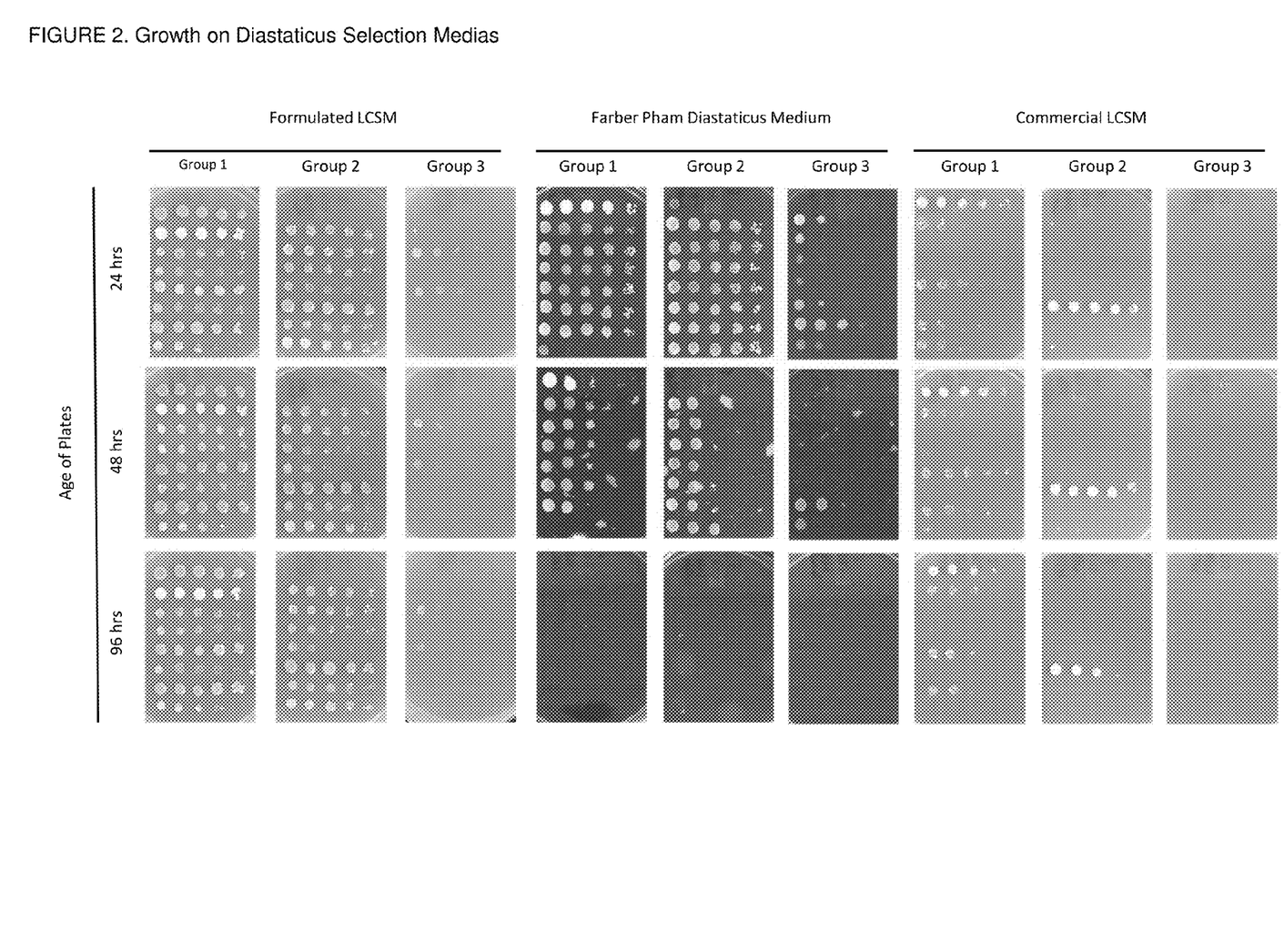
FIG. 2 depicts growth from serial dilutions as described in the Example on Formulated LCSM, Farber Pham *Diastaticus* Medium, and Commercial LCSM media. Plates were autoclaved and poured 24 hrs, 48 hrs or 96 hrs prior to plating serial dilutions.

To assess the recovery rates and background growth of sta– strains, serial dilutions were performed. All strains were plated on YPD to represent non-selective conditions controlling for equal plating and comparable growth rates (FIG. 1). STA+ and UAS+ genotyping of the OYL strains was determined by PCR (Table I). The strains were grouped as follows: STA+/UAS+(Group I), STA+/uas– (Group II), and strains having high levels of background when copper sulfate concentrations are reduced (Group Ill). FIG. 2 illustrates the comparison of commercial LCSM, FPDM, and the Formulated LCSM generated as described above. Commercial LCSM was the most stringent selection media with recovery of <50% of the tested STA+ strains (OYL-026, OYL-033, OYL-112, OYL-500, OYL-501 and OYL-042)

and no background growth of sta− strains. Commercial LCSM also resulted in a lower limit of detection with 0.5-20% recovery rates in OYL-033, OYL-112, OYL-500, and OYL-501. FPDM exhibited the greatest effect of plate aging with ~36-fold less cell growth from 24 to 48 hrs, with no permissible growth after 96 hrs. Manufacturers advise using plates within 24 hrs of pouring. FPDM also showed the highest background growth with 100% of the Group III sta− strains exhibiting growth at the 1 million/ml plated cell density. With the Formulated LCSM produced as described above, all tested STA+ strains were recovered. With the exception of OYL040, 100% recovery was observed to the last serial dilution spot (~3 cells) if used within 48 hrs. The media minimizes background growth, but there is low-level, leaky growth of sta− OYL-024 and OYL-030 Belgian strains. The Formulated LCSM (produced as described above) is effective after 96 hrs, but shows slightly higher stringency.

In view of these results, LCSM is a suitable selection media for STA+ strains; however, attention should be paid to the cupric sulfate and dipotassium ortho-phosphate concentrations, autoclave cycling, age of the plates and the potential for sta− background observed in a limited number of Belgian strains. Of note, the STA+ selection medias showed no difference in growth between UAS+ and uas− strains; thus, further methods were explored for characterizing and phenotyping the difference between these STA+ strains.

Phenotyping STA+ strains with Maltodextrin and Dextrin III Starch Degradation Assays: Few methods exist for the phenotypic evaluation of the diastatic activity of STA+ strains (Meier-Dörnberg et al. *FEMS Yeast Res*, 18(4), foy023 (2018); Krogerus et al., supra). Diastatic activity varies widely and recently has been shown to strongly correlate with a naturally occurring −1162 bp deletion of the STA1 promoter region (Krogerus et al., supra). Brewers are faced with a decision to recall or destroy beer that has a confirmed STA1+ PCR result or a contaminant that shows copper sulfate resistance, but real risk of this result leading to re-fermentation and exploding bottles is unknown. To help breweries assess risk, the assays disclosed herein were developed that confirm diastatic activity with a relatively quick turnaround and which differentiate between strains with high and low diastatic risk.

Figure 3A:
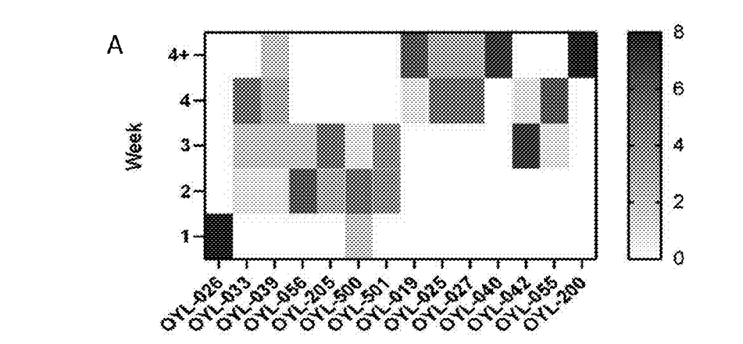
FIG. 3A is a heat map illustrating the number of weeks required for various strains to reach <50% dextrin III degradation.

The first assay relies on pH change as an indicator of growth and a readout of maltodextrin fermentation. The second assay is a method for characterizing the potential risk of the different diastatic *S. cerevisiae* strains. The STA+ strain collection and a sta− control (OYL-088) were assayed for starch degradation over time. Colonies were cultured overnight with agitation in YPGE+2% Dextrin III media to promote growth while relieving any glucose repression of STA1 transcription. The cultures were then left still on the benchtop for up to a month to monitor Dextrin III degradation. Iodine was used to detect the remaining Dextrin III in each sample using UV absorbance at 540 nm and 680 nm as a readout for amylose and amylopectin, respectively. Summarized in FIG. 3A is the timing of starch breakdown in the various STA+ strains. Several highly diastatic strains such as OYL-026, OYL-056, OYL-205, OYL-500, and OYL-501 were able to degrade >50% of the Dextrin III by week 2. These strains also contain an intact STA1 promoter region (UAS+) and, thus, are predicted to have higher STA1 expression and diastatic activity. This observation was not uniform among UAS+ strains, as OYL-033 and OYL-039 typically took up to three weeks to degrade >50% of the Dextrin Ill.

Figure 3B:
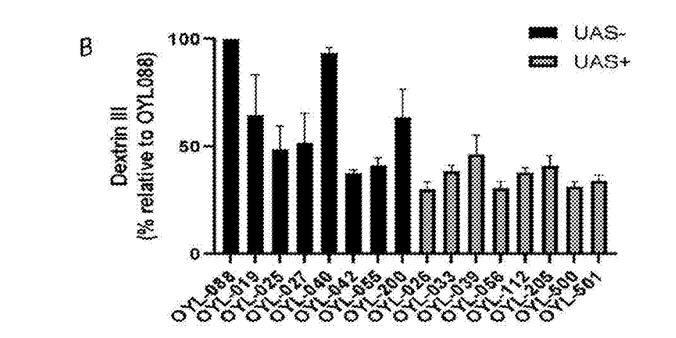
FIG. 3B is a bar graph illustrating the amount of dextrin Ill remaining relative to OYL-088 control.
Figure 3C:
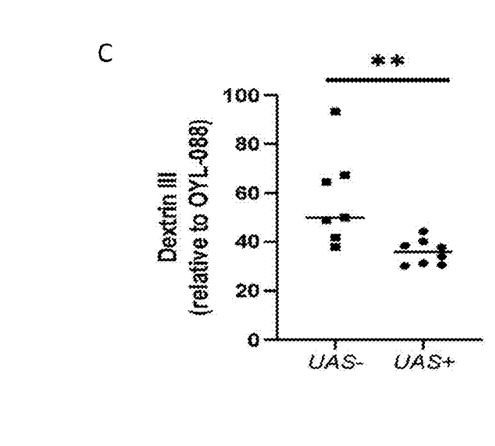
FIG. 3C illustrates dextrin III degradation in UAS− and UAS+ strains relative to OYL-088 control (**p<0.005 by student's t-test).
Figure 3D:
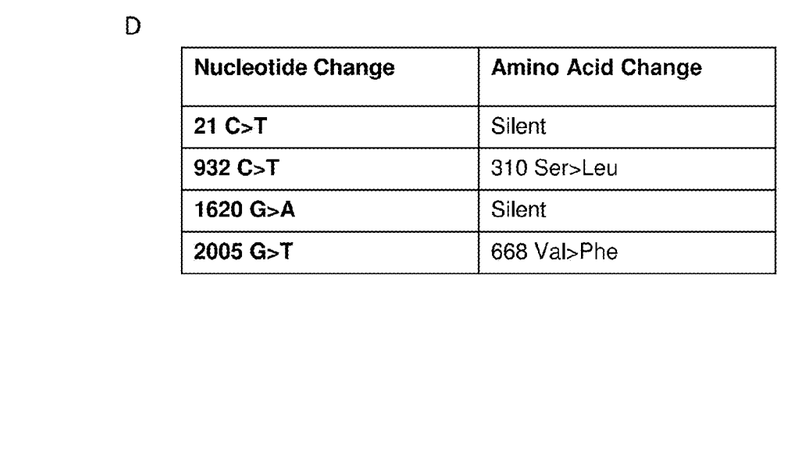
FIG. 3D is a chart describing the amino acid change associated with various nucleic acid substitutions as described in the Example.

Variation in diastatic activity was observed in uas− strains, with OYL-042 showing starch breakdown by three weeks and other strains such as OYL-019, OYL-200 and OYL-040 rarely reaching >50% dextrin breakdown by week 4. In fact, when the assay was terminated, the average starch breakdown of OYL-040 was 93% (FIG. 3B). OYL-019, OYL-040, and OYL-200 measurements were carried out to 8 weeks to investigate this further. OYL-040 was further sequenced to identify additional sequence variants that may result in the observed lower diastatic activity. The sequencing identified several single nucleotide polymorphisms within the coding sequence of the STA1 gene (FIG. 3D). While two of the SNPs are silent and do not result in amino acid changes, the other two (932 C>T and 2005 G>T) result in amino acid changes of 310aa Ser>Leu and 668aa Val>Phe, respectively.

The two liquid based assays described above have the advantages of being inexpensive and accessible for brewery labs. The range of diastatic activity in STA+ strains strongly correlation to the STA+ promoter status. These phenotyping assays are useful, e.g., for assessing the risk of a contaminant to inform decisions to destroy beer or recall product due to contamination.

A Co-culture Assay to Functionally Score The Promoter Status of STA+ Strains: A major risk that STA+ strains pose to packaged beer is the potential for a small amount of STA+ cells to secrete the glucoamylase enzyme, which then degrades starch and provides simple sugars for yeast to ferment. This premise was used to design a co-culture assay to score diastatic activity. STA+ strains were patched adjacent to sta− strain on plates containing maltodextrin as the sole carbon source and scored for STA+ supported growth of the sta− strain. If the STA+ strain secreted high levels of Sta1 protein, the enzyme breaks down the maltodextrin and supports the growth of a sta− strain. The sta− strain used was the lab strain W303 containing the ade2-1 allele, which results in the accumulation of the intermediate metabolite P-ribosylaminoimidazole carboxylate (red pigment) into vacuoles and the development of red colonies. This strain choice helped differentiate between robust growth (red), intermediate growth (red-white gradient), and slow growth (white) of the sta− strain. The STA+ strains were assayed and the results are summarized in Table 2.

TABLE 2

Soring of STA+ Strains in Maltodextrin Co-culture Assay

| Strain | UAS | Day 3 | Day 7 | Day 8 | Day 10 | Day 30 |
| --- | --- | --- | --- | --- | --- | --- |
| OYL-088 | − | − | − | − | − | − |
| OYL-019 | − | − | + | + | + | + |
| OYL-025 | − | − | + | + | + | + |
| OYL-027 | − | + | +++ | +++ | +++ | +++ |
| OYL-040 | − | − | − | − | − | − |
| OYL-042 | − | + | + | +++ | +++ | +++ |
| OYL-055 | − | + | +++ | +++ | +++ | +++ |
| OYL-200 | − | − | + | + | + | +++ |
| OYL-026 | + | +++ | +++ | +++ | +++ | +++ |
| OYL-033 | + | + | +++ | +++ | +++ | +++ |
| OYL-039 | + | + | +++ | +++ | +++ | +++ |
| OYL-056 | + | + | +++ | +++ | +++ | +++ |
| OYL-112 | + | + | +++ | +++ | +++ | +++ |

TABLE 2-continued

Soring of STA+ Strains in Maltodextrin Co-culture Assay

| Strain | UAS | Day 3 | Day 7 | Day 8 | Day 10 | Day 30 |
|---|---|---|---|---|---|---|
| OYL-205 | + | + | +++ | +++ | +++ | +++ |
| OYL-500 | + | +++ | +++ | +++ | +++ | +++ |
| OYL-501 | + | − | ++ | ++ | +++ | +++ |

Key:
− No difference to OYL-088;
+ Growth of STA+ strain;
++ Growth of STA+ strain and W303;
+++ Growth of STA+ strain and color change in W303.

Figure 4A:
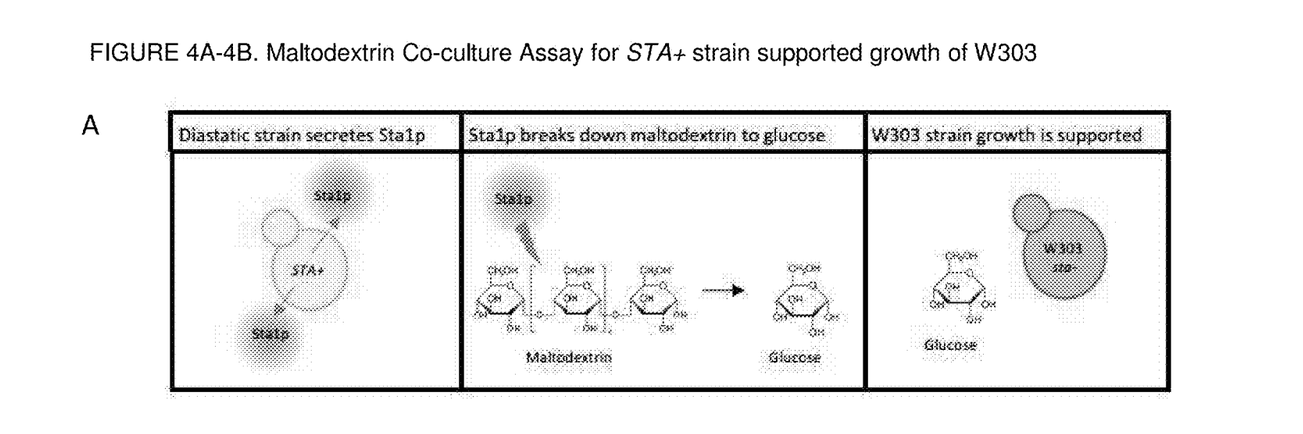
FIG. 4A is a schematic of the dextrin co-culture assay.
Figure 4B:
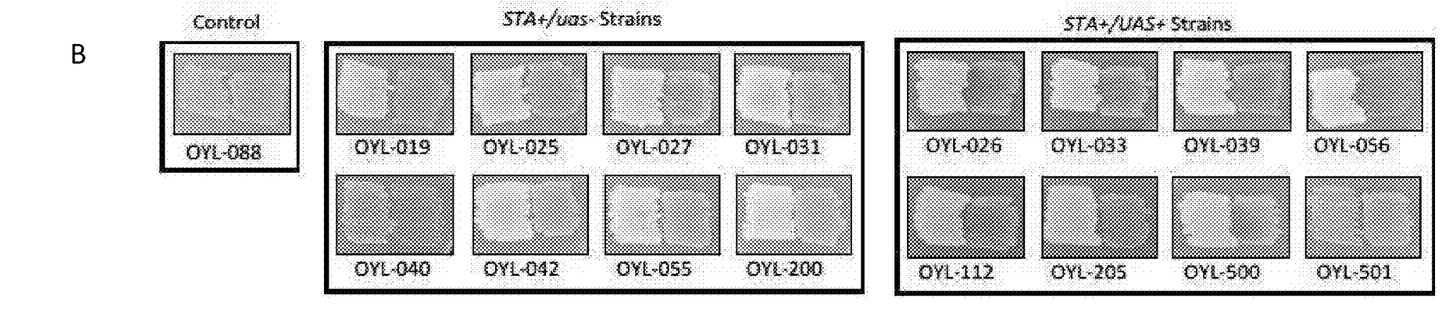
FIG. 4B depicts growth on maltodextrin co-culture plates after 10 days. On each plate, a STA+ strain was plated on the right and the sta− W303 strain was plated on the left. Red colony growth of W303 is an indicator of the diastatic activity of the adjacent STA+ strain.
Figures 4C, 4D:
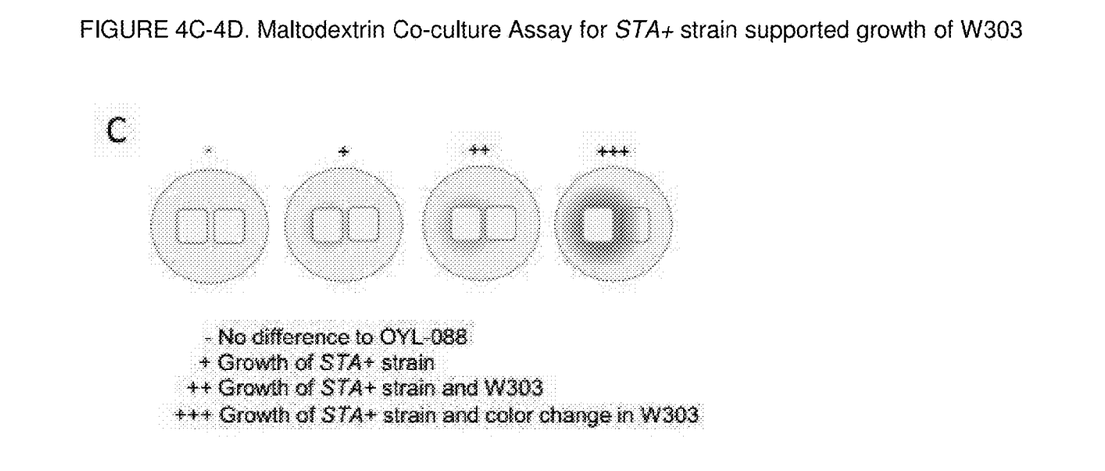
FIG. 4C illustrates a scoring system for the dextrin co-culture assay.
FIG. 4D depicts the limit of detection of the dextrin co-culture assay. OYL-026 culture was diluted 1:10 in OYL-088 culture, enriched in liquid LCSM, and plated.
Figure 4D:
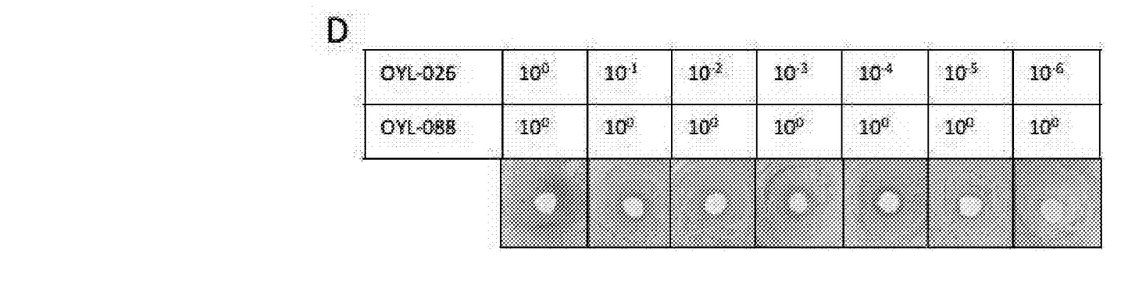

In just one week of growth, the STA+/UAS+ strains were able to support intermediate to robust growth of the W303 strain, whereas the STA+/uas− only showed enhanced growth relative to the sta− control, OYL-088 (FIG. 4A). Growth was scored again after 30 days and still the STA+/uas− strains were unable to provide enough fermentables to induce color change in the W303 (FIG. 4B). These results correlate very well to the Dextrin III liquid assay (FIG. 3) and, again, OYL-040 was the least diastatic relative to the STA+/uas− strains. Robust growth of the W303 sta− strain strongly differentiates between STA+ strains with intact promoters and the 1162 b.p. deletion. Therefore, this assay can be used to confirm the presence of suspected contaminant to further differentiate the promoter status.

The limit of detection of this assay was assessed as a method for screening yeast slurries, propagations, or enriched beer samples. The culture/slurry was spotted onto a lawn of W303 cells and color change was scored at the perimeter of the spot. Unfortunately, not all strains exhibited robust enough diastatic activity to resolve contaminants below 1 million cells/ml. An enrichment approach in liquid LCSM media was employed to test this further. Overnight saturated YPGE cultures were diluted into liquid LCSM for a 24 hr enrichment. OYL-026 was serially diluted 1:10 into OYL-088 inoculated cultures. The lowest dilution volume 10-6 corresponds to 200 cells/ml of OYL-026 and 200×10$^6$ cells/ml of OYL-088. A color change in W303 indicating the presence of OYL-026 was observed down to the 10$^{-6}$ dilution. This approach was able to detect a contaminated mock-propagation (FIG. 4C). The turnaround of this assay, however, was 7-9 days.

Figures 5A, 5D:
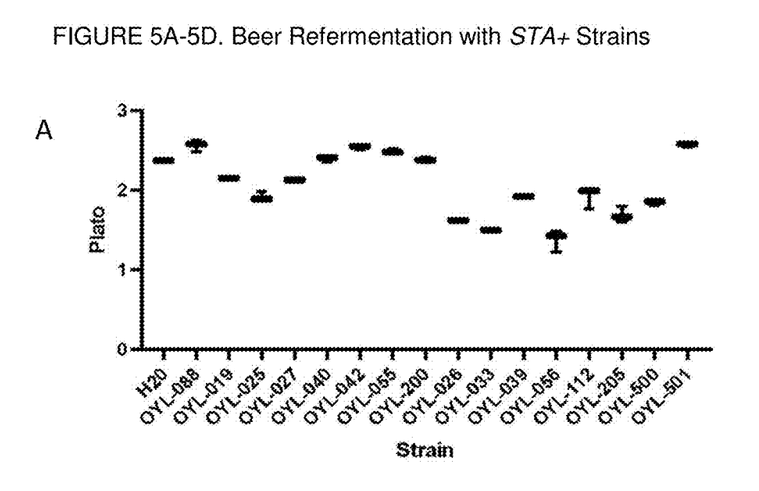
FIG. 5A depicts plato measurements of each referenced strain after one month in IPA inoculated with 3 million cells/bottle.
FIG. 5D depicts plato measurements after inoculation of OYL026, OYL-027, OYL042 and OYL-056 at varying concentrations.
Figure 5B:
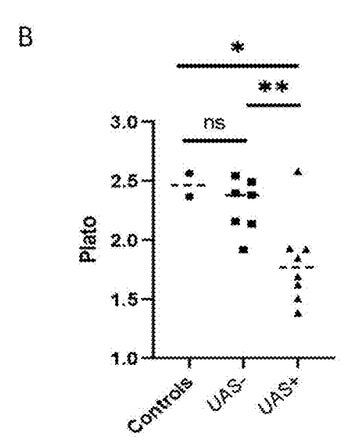
FIG. 5B depicts plato measurements grouped into control, UAS+, and UAS− strains. (ns=not significant, *p<0.05, **p<0.005 by one-way ANOVA).
Figure 5C:
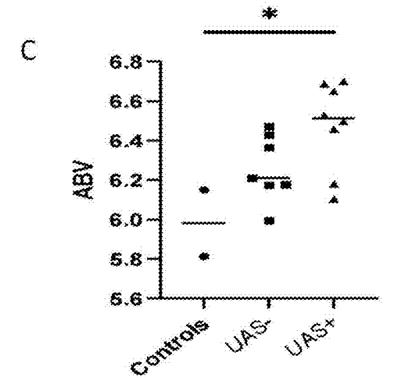
FIG. 5C depicts alcohol by volume (ABV) grouped into control, UAS+ and UAS-strains. (*p<0.05 by one-way ANOVA).
Figure 5D:
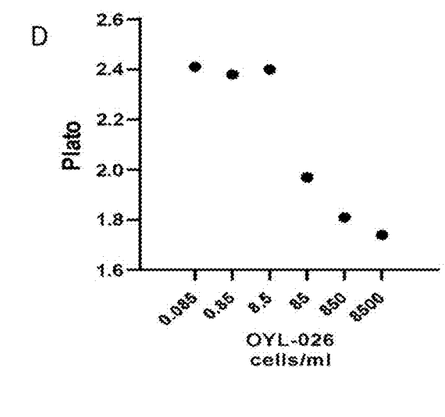

Bottle Re-fermentations Assess Diastatic Activity in Packaged Product: The phenotypic assays described here strongly suggest that there are high risk and low risk STA+ strains. To test this in packaged beer, STA+ strains were inoculated into a IPA (India Pale Ale) bottles to mimic contamination at packaging. The IPA was chosen as a representative ale, with a 2.6° P residual extract, moderate hopping rate, and 6.2% abv. One month post-inoculation, OYL-026, OYL-033, and OYL-056 strains lowered the residual extract to 1.4-1.6P (FIG. 5A). This represents an addition of two volumes of $CO_2$ in the packaged product, which at room temperature is above the pressure rating for a glass beer bottle and a significant hazard. The remaining STA+/UAS+ strains, excluding OYL-501, were >0.6° P below the OYL-088 control. OYL-501 was likely less active due to the health of the inoculant culture. Interestingly, the residual extracts in OYL-019, OYL-025, and OYL-027 were also lowered by 0.4-0.6P (FIG. 5A) despite the 1162 b.p. promoter deletion and the lower diastatic activity observed in the maltodextrin and starch-degradation assays. At this high rate of inoculant (>3000 cells/ml) these STA+/uas− strains still pose a re-fermentation risk. The mean Plato and ABV of STA+/UAS+ and STA+/uas+ were compared to the control OYL-088 and mock water inoculation (FIGS. 5B and 5C). The STA+/UAS+ strains were significantly lower in Plato, whereas the STA+/uas+ strains were not. Thus, collectively the STA+/UAS+ strains pose significantly more risk to packaged product.

To determine the minimum dose (CFU/ml) that results in re-fermentation of the packaged beer within a month, bottles were inoculated with 10-fold dilutions of the most potent STA+/UAS+ strains, OYL-026 and OYL-056, and the STA+/uas− strains, OYL-042 and OYL-027 (FIG. 5D). After 1 month, the minimum dose of 10 cells/ml was sufficient for the STA+/UAS+ strains to re-ferment; however, this dose did not result in re-fermentation for STA+/UAS+ strains. Over extended periods of time, lower doses may result in re-fermentation. Also, the composition of the beer will have an impact on this as well.

The Example provides a comprehensive analysis of selection medias for diastatic *S. cerevisiae* strains using a collection of STA+ strains. Further, variation in diastatic activity across STA+ strains was observed, showing a correlation with earlier onset and increasing strength in strains that contain an intact promoter (STA+/UAS+). The Example also describes a robust plate-based assay for the functional risk assessment of diastatic *S. cerevisiae* contamination. The functional assay described herein addresses a long-felt need for quality control with respect to diastatic *S. cerevisiae* contaminations in breweries. The results of the assay described herein can be used to assess the risk of re-fermentation in packaged product with the potential for determining contaminant thresholds for different STA+ strains and inform decisions to sacrifice beer before packaging or issue a product recall.

What is claimed:

1. A culture plate comprising medium which supports microbial growth and comprises a dextrin comprising four or more glucose units linked by $\alpha(1\rightarrow4)$ glycosidic bonds as a sole carbon source, wherein the culture plate comprises a first zone inoculated with a sta− *Saccharomyces cerevisiae* strain which produces a pigment upon sugar fermentation, and a second zone adjacent to the first zone and which is not inoculated with a microbe.

2. The culture plate of claim 1, wherein the dextrin is maltodextrin, dextrin commercial type I, dextrin commercial type II, dextrin commercial type III, potato starch, corn starch, tapioca starch, amylose, or amylopectin.

3. The culture plate of claim 2, wherein the dextrin is maltodextrin.

4. The culture plate of claim 1, wherein the medium comprises 0.1%-20% dextrin.

5. The culture plate of claim 4, wherein the medium comprises 0.5%-10% dextrin.

6. The culture plate of claim 5, wherein the medium comprises 1-4% dextrin.

7. The culture plate of claim 6, wherein the medium comprises 2% dextrin.

8. The culture plate of claim 1, wherein the medium comprises yeast nitrogen base (YNB)+ nitrogen, SC-Complete mix, and agar.

9. The culture plate of claim 1, wherein the sta− *S. cerevisiae* strain comprises the ade2-1 allele, a deletion or inactivating mutation in ade1, or a deletion or inactivation mutation in ade2.

10. The culture plate of claim 1, wherein the sta− *S. cerevisiae* strain expresses a non-native pigment.

11. The culture plate of claim 1, wherein the sta– *S. cerevisiae* strain is W303 MATa {leu2-3,112 trp1-1 can1-100 ura3-1 ade2-1 his3-11,15}.

12. The culture plate of claim 1, wherein the microbe is yeast.

13. The culture plate of claim 12, wherein the yeast is *S. cerevisiae*.

14. A method of characterizing microbial diastatic activity, the method comprising inoculating the second zone of the culture plate of claim 1 with a microbe sample, incubating the plate under conditions which allow growth of *S. cerevisiae* and the microbe, and identifying growth of the sta– *S. cerevisiae* strain, wherein growth of the sta– *S. cerevisiae* strain indicates the presence of diastatic activity in the microbe sample.

15. The method of claim 14, further comprising detecting pigmented colonies in the first zone of the culture plate, wherein the presence of pigmented colonies indicates the presence of diastatic activity in the microbe sample.

16. The method of claim 14, comprising incubating the culture plate for at least three days.

17. The method of claim 16, comprising incubating the culture plate for about one week.

18. The method of claim 16, comprising incubating the culture plate for about one month.

19. The method of claim 14, comprising incubating the culture plate for no longer than about one month.

20. The method of claim 14, wherein the microbe is yeast.

21. The method of claim 20, wherein the yeast is *S. cerevisiae*.

\* \* \* \* \*